United States Patent [19]

Lundblad

[11] Patent Number: 4,919,961
[45] Date of Patent: Apr. 24, 1990

[54] LACTO-N-TETRAOSE CONTAINING FOOD-STUFF AND A PROCESS FOR ITS PREPARATION

[75] Inventor: Arne Lundblad, Bytaregatan, Sweden
[73] Assignee: Biocarb AB, Sweden
[21] Appl. No.: 259,745
[22] Filed: Oct. 19, 1988

[30] Foreign Application Priority Data

Oct. 22, 1987 [SE] Sweden ................................. 8704115

[51] Int. Cl.$^5$ ............................. A23C 9/13; A23L 1/30
[52] U.S. Cl. ........................................ 426/580; 426/71; 426/588; 426/648; 426/801
[58] Field of Search ................. 426/71, 580, 588, 801, 426/648

[56] References Cited

U.S. PATENT DOCUMENTS 2,710,807  6/1955  György et al. ........................ 426/71

FOREIGN PATENT DOCUMENTS 223972  10/1959  Australia ................................ 426/71

OTHER PUBLICATIONS

"Inhibition of Attachment of Streptococcus pneumoniae and *Haemophilus influenzae* by Human Milk and Receptor Oligosaccharides", by Bengt Anderson et al, Journal of Infectious Diseases, vol. 153, No. 2, pp. 232 to 237, Feb., 1986.

*Primary Examiner*—Donald E. Czaja
*Assistant Examiner*—Helen Pratt
*Attorney, Agent, or Firm*—Burns, Doane, Swecker & Mathis

[57] ABSTRACT

Food-stuff, particularly based on ruminants milk, having added thereto Lacto-N-tetraose in a gastro-intestinally effective amount; and a process for its preparation.

12 Claims, No Drawings

LACTO-N-TETRAOSE CONTAINING FOOD-STUFF AND A PROCESS FOR ITS PREPARATION

The present invention relates to food-stuffs to which there has been added an oligosaccharide having beneficial effect on the bacterial flora of the gastro-intestinal tract.

It is a well-known fact that humans including children and babies are fed with milk or milk products from other species than homo, particularly milk from herbivorous animals, mainly ruminants. The excessive intake of such milk products frequently results in disturbance in the bacterial flora of the gastro-intestinal tract, and particularly when feeding human infants during the sucking period with such milk products in addition to or instead of natural mother's milk usually causes problems.

Bacteria inhabit the gastro-intestinal tract in large numbers. The bacterial flora varies in different parts of the intestines and varies with age. Likewise, the flora differs in infants who are fed on breast milk as compared to those who are bottle-fed. The reasons for these differences are largely unknown. In addition to the qualitative difference in flora between breast-fed and bottle-fed children there appears to exist a well documented difference in susceptibility to microbial infection. Thus, breast-fed children are more resistent to gastro-intestinal infection than are bottle-fed children. This difference has been considered to be attributed to the presence of specific immunoglobulines in breast milk, but this has never been adequately documented to be the sole reason. On the contrary there is mounting evidence that othe factors in breast milk like lactoferrin, glycolipids, glycoproteins and oligosaccharides play an important role.

The present invention has for a main object to provide food-stuffs which have a beneficial effect on the gastro-intestinal bacterial flora.

Another object of the invention is to provide for food-stuffs based on milk originating from ruminants. The invention also has for an object to provide a process for preparing such food-stuff. In connection with research and experimentation it has surprisingly been found that the main reason for the difference in the effect of different food-stuffs on the bacterial flora of the gastro-intestinal tract resulting inter alia in differing susceptibility to infections is attributed to a single compound which is found in human milk but not in ruminant's milk. This compound is an oligosaccharide, Lacto-N-tetraose (LNT) having the following structure D-galactopyranosyl $\beta$-(1-39-2-acetamido-2-deoxy-D-glucopyranosyl-$\beta$(1-3)D-galactopyranosyl-$\beta$-(1-4)-D-glucopyranose also abbreviated:

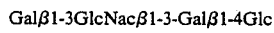

Gal$\beta$1-3GlcNac$\beta$1-3-Gal$\beta$1-4Glc

This oligosaccharide is a known compound and can be isolated in a manner known per se from pooled human milk or produced by chemical synthesis.

Accordingly, the present invention provides for a food-stuff having added thereto Lacto-N-tetraose in a gastro-intestinal effective amount.

Such food-stuff is preferably based on milk of ruminative origin, such as bovine origin, and is preferably based on milk or dairy cow origin. The food-stuff is not human milk.

The effective amount of Lacto-N-tetraose to be taken orally together with some desirable food-stuff may vary within broad limits, but it is preferred to have a daily intake of Lacto-N-tetraose of about 0.1 to about 20 g.

As indicated above the food-stuff is preferably milk or milk-powder, and when using milk in a liquid form it preferably contains about 0.1 to 0.5 g of Lacto-N-tetraose per liter.

A preferred food-stuff according to the invention is constituted by pasteurized and dried ruminants milk in powdery form having admixed therein Lacto-N-tetraose in a quantity corresponding to the daily intake or milk concentration as indicated above.

The process for preparing such food-stuff is simply constituted by mixing a conventional food-stuff, such as milk, with gastro-intestinally active amount of Lacto-N-tetraose to result in the desired product.

In a preferred embodiment of such process milk or ruminative origin is pasteurized and dried, such as by spray-drying, to form a milk powder and said powder is then mixed with Lacto-N-tetraose to form a mixture which is storage stable and provides for facile distribution. The mixture obtained can be reconstituted with water to form the desired liquid product ready for use. The milk used is preferably of bovine origin.

Although the present invention will be mainly illustrated with reference to milk-based products the invention is applicable to all kinds of food-stuffs, i.e. solid, semi-solid and liquid ones. The beneficial effect of the oligosaccharide on the bacterial flora will be obtained irrespective of the type of food-stuff it is associated with.

The present invention will in the following be further described by non-limiting examples.

EXAMPLE 1

Ordinary dairy cows milk is pasteurised and spray-dried in a conventional manner to form a milk powder. The resulting powder is then mixed with Lacto-N-tetraose together with any other desirable conventional ingredients. The resulting mixture of formula is then reconstituted with water to result in reconstituted milk having a concentration of about 3 g Lacto-N-tetraose per liter.

Two groups of human infants are fed with reconstituted milk with or without Lacto-N-tetraose. Group 1 was given reconstituted milk containing the oligosaccharides, whereas Group 2 was given the same reconstituted milk but without any contents of Lacto-N-tetraose.

During the experimental period faeces from the infants were collected for chemical and bacteriological analysis. It was found that the infants of Group 1 produced oligosaccharides containing the basic structure of Lacto-N-tetraose, whereas the infants of Group ;b 2 did not. Moreover, the bacterial flora in faeces was much more stable with regard to Group 1 than with regard to Group 2. Furthermore, the infants of Group 2 were in many cases subject to diarrhea, which was not the case with the infants of Group 1.

EXAMPLE 2

Adding about 10 g Lacto-N-tetraose per day to the daily food intake of adults results in significant improvement of the gastro-intestinal conditions as indicated by improved well-being.

I claim:

1. Food-stuff having added thereto Lacto-N-tetraose in an amount effective to stabilize bacterial flora in faeces, said lacto-N-tetraose being of synthetic origin or isolated from human milk, said food-stuff not being human milk.

2. Food-stuff according to claim 1 constituted by milk of ruminative origin.

3. Food-stuff according to claim 2, wherein the milk is of dairy cow origin.

4. Food-stuff according to claim 1, wherein said effective amount is such as to result in a daily intake of Lacto-N-tetraose of about 0.1 to about 20 g.

5. Food-stuff according to claim 2 or 3, wherein the milk contains about 0.1 to 0.5 g of Lacto-N-tetraose.

6. Food-stuff according to claim 1 constituted by pasteurized and dried ruminants milk in powdery form.

7. A process for preparing the food-stuff according to claim 1, comprising mixing a conventional food-stuff with an amount of Lacto-N-tetraose effective to stabilize bacterial flora in faeces, said Lacto-N-tetraose being of synthetic origin or isolated from human milk.

8. A process according to claim 7, wherein said food-stuff is milk of ruminative origin and further comprises pasteurizing said milk and drying the resulting milk to form a milk powder, mixing said powder with Lacto-N-tetraose and reconstituting the mixture obtained with water to form the desired product.

9. A process according to claim 8, wherein the milk is of bovine origin.

10. Food-stuff according to claim 2, wherein said effective amount is such as to result in a daily intake of Lacto-N-tetraose of about 0.1 to about 20 g.

11. Food-stuff according to claim 3, wherein said effective amount is such as to result in a daily intake of Lacto-N-tetraose of about 0.1 to about 20 g.

12. Food-stuff according to claim 3, wherein the milk contains about 0.1 to 0.5 g of Lacto-N-tetraose.

* * * * *